United States Patent [19]
Fox et al.

[11] Patent Number: 5,358,525
[45] Date of Patent: Oct. 25, 1994

[54] BEARING SURFACE FOR PROSTHESIS AND REPLACEMENT OF MENISCAL CARTILAGE

[76] Inventors: John E. Fox, 11 Hickory Trail, Lake Mohawk, Sparta, N.J. 07871; Stephen J. Fox, 3 Ridgewood La., Concord, N.H. 03301

[21] Appl. No.: 998,184

[22] Filed: Dec. 28, 1992

[51] Int. Cl.$^5$ ................................. A61F 2/30
[52] U.S. Cl. ............................ 623/18; 623/20
[58] Field of Search .............. 623/7, 8, 11, 12, 16, 623/17, 18

[56] References Cited

U.S. PATENT DOCUMENTS

| | | | |
|---|---|---|---|
| 3,986,213 | 10/1976 | Lynch | 623/8 |
| 4,467,479 | 8/1984 | Brody | 623/18 |
| 4,911,718 | 3/1990 | Lee et al. | 623/18 |
| 4,919,667 | 4/1990 | Richmond | 623/18 |
| 4,919,668 | 4/1990 | Rosenbaum et al. | 623/18 |
| 5,192,326 | 3/1993 | Bao et al. | 623/17 |

Primary Examiner—David Isabella
Attorney, Agent, or Firm—William B. Ritchie

[57] ABSTRACT

A cartilage replacement apparatus. This apparatus is a hollow plastic pad with a load bearing material within the plastic pad. The load bearing surface provides the shock absorbing compliance of natural cartilage and is effective in absorbing the peak contact stresses imposed on a prosthesis when placed in an extreme, load bearing situation. The unique characteristics of the invention makes it a permanent replacement for cartilage, thus permitting patients to avoid further replacement surgery. It also would provide a unique bearing surface for total joint replacement surgery, such that it would obviate the destructive effects of particulate debris.

9 Claims, 5 Drawing Sheets

BEARING SURFACE FOR PROSTHESIS AND REPLACEMENT OF MENISCAL CARTILAGE

BACKGROUND OF THE INVENTION

1. Field of the Invention

The invention relates to bearing surfaces in cartilage replacement and total joint replacement.

2. Description of the Related Art

Normal meniscal and articular cartilage have natural properties of compliant conformity with the load bearing bone surfaces. Through unique hydrodynamics, natural cartilage provides a bearing and shock absorbing surface that normally serves an individual for a lifetime. Injury and disease can lead to the need to remove the natural cartilage, and often, the entire joint through an arthroplasty procedure.

Prior art has shown many prosthetic designs and configurations which address the restoration of joint function and biocompatibility. The prior art prosthesis designs either ignore the need for artificial cartilage or, more frequently, address the need with material that provides thickness, strength and a low coefficient of friction. This rigid material has lacked the shock absorbing compliance of natural cartilage and has been ineffective in absorbing the peak contact stresses imposed on a prosthesis when placed in an extreme, load bearing situation.

Repeated exposure to these extreme situations has resulted in particulate wear of the pad and resultant debris. This wear and particulate debris inevitably leads to failure of the prosthesis through pitting and dissolution of the surrounding bony architecture via an inflammatory reaction to the debris. The resultant dissolution of the bony architecture compromises the potential of subsequent prosthetic implantation.

The prior art does not disclose a prosthetic design which provides a lasting replacement for human cartilage or lasting bearing surface for total joint arthroplasty.

SUMMARY OF THE INVENTION

It is an object of the invention to provide a lasting replacement for human cartilage.

It is another object of the invention to provide an improved bearing surface for prosthetic replacements.

The invention is a cartilage replacement apparatus. A pad of pliable and compliant shock absorbing material with a hollow interior is provided. Load bearing material which fills the interior of said pad, and is capable of movement in response to varying load vectors applied to said pad is provided, wherein, said pad with said load bearing material is capable of self-modulation, congruency and shock absorbency in a manner similar to actual cartilage.

DETAILED DESCRIPTION OF THE INVENTION

Figure 1:
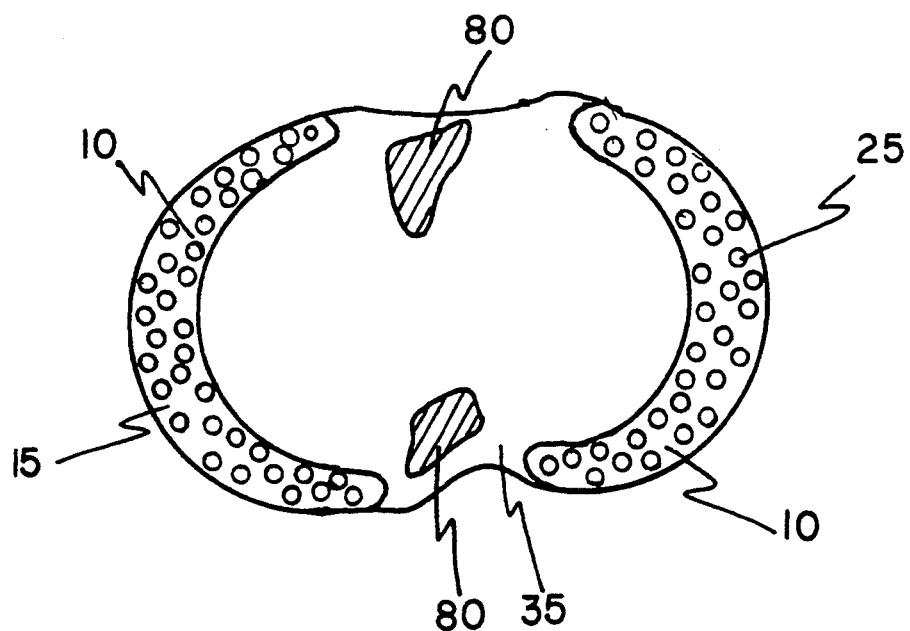
FIG. 1 is a cross-section of the cartilage replacement pads on the tibia.

FIG. 1 is a cross-section of the cartilage replacement pads 10 on the tibia 35. Within tibia 35 are cruciate ligaments 80. In a complete or partial meniscal cartilage replacement, the lateral meniscus 15 or medial meniscal 20 will be replaced by cartilage replacement pads 10. The cartilage pads 10 are preferably 15-20% the size of the related bone structure, and approximately ½ inch thick in a triangular shape. The cartilage replacement pads 10 are constructed of hollow ultra high molecular weight polyethylene plastic filled with a load bearing material 25. The load bearing material 25 may be numerous small ball bearings. Preferably, all the ball bearings should be substantially the same size, between 1-2 millimeters, with approximately 2-3 ball bearings per square millimeters. The ball bearings 25 would be preferably constructed of surgical-grade stainless steel coated with silicon or other lubricant. The ball bearings 25 are capable of shifting positions within the hollow interior of the cartilage replacement pads as varying load vectors are applied.

Alternatively, the load bearing material 25 could also be a gelatinous fluid that is well known in the art as being compatible with biological systems. This fluid serves to act as a load bearing material based on standard vertical and horizontal displacement hydrodynamics. The load bearing material 25, allows the cartilage replacement pads 10 to remain pliable, compliant, and shock absorbing. This minimizes the peak contact pressures and the resultant particulate wear, thus allowing the cartilage replacement to act in the same manner as human cartilage.

This ability of the cartilage replacement pads 10 to effectively simulate actual cartilage will avoid future replacement of the cartilage replacement pads 10, and allow the joint replacement to be permanent. The cartilage replacement pads 10 are capable of self-modulation, congruency and shock absorbency like that of human cartilage.

The cartilage replacement pads 10 are fabricated from an injection molding procedure. The bearing material 25 is inserted into the hollow cartilage replacement pad cavity.

Figure 2:
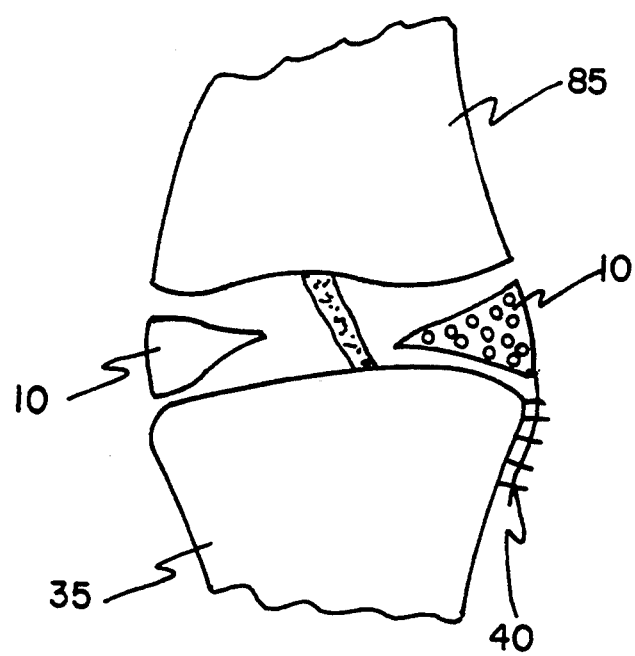
FIG. 2 is a frontal view of the cartilage replacement pads used in a knee.

FIG. 2 is a frontal view of cartilage replacement pads 10 used in a knee at a location between tibia 35 and femur 85. The cartilage replacement pads 10 will have an apron 40 comprising non-absorbent biocompatible material, preferably polyethylene plastic or other non-absorbent material, molded to the cartilage replacement pad 10. The cartilage replacement pad 10 may also be secured with a direct suture or staple. The location of the apron 40 will be the lower, exterior edge of the cartilage replacement pad 10. Security in the placement of the cartilage replacement pads 10 will be provided by stapling the apron 40 to the tibia 35 with a bone staple or suture well known in the art.

Figure 3:
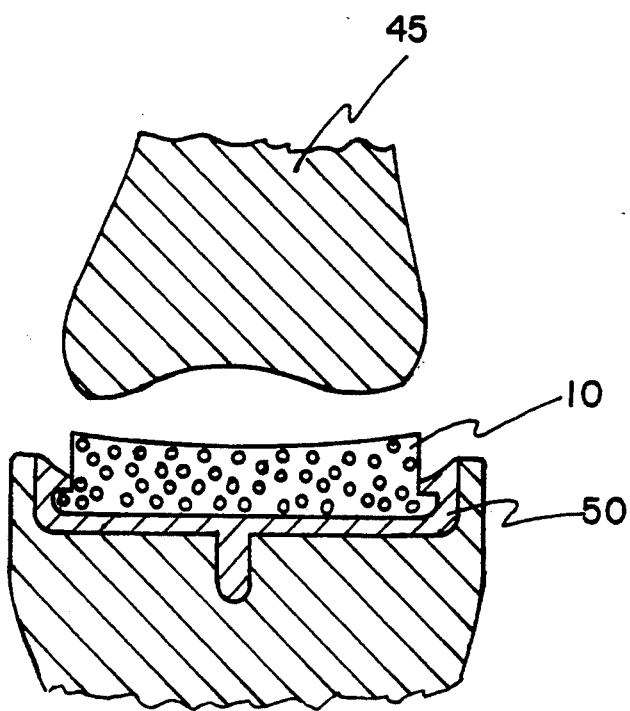
FIG. 3 is a frontal view of a knee arthroplasty with cartilage replacement pads.

FIG. 3 is a frontal view of a knee arthroplasty. A cartilage replacement pad 10, will be inserted between the femoral component 45 of the prosthesis and the tibial component 50 of the prosthesis on the tibia 35. Security for the positioning of the cartilage replacement pad 10 will be provided by molded posts, slots, straps or screw holes within the tibial component integral to the molding of the cartilage replacement pad 10 which lock the pad to the tibial component.

Figure 4:
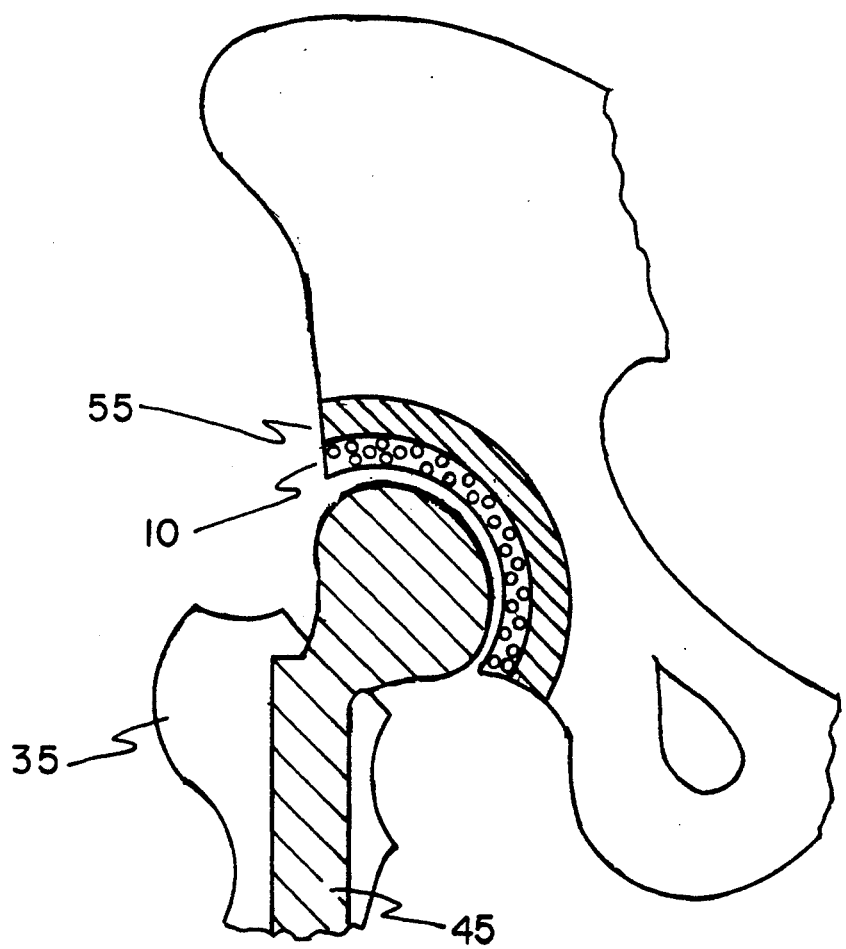
FIG. 4 is a front view of a hip arthroplasty with cartilage replacement pads.

FIG. 4 is a front view of a hip arthroplasty. The cartilage replacement pad 10 is inserted between the femoral component 45 of the prosthesis and the acetabular component 55 of the prosthesis and locked into the acetabular component in a mechanism similar to that of the tibial component of the knee. The femoral component 45 is inserted into femur 35. The acetabular component 55 is secured to the acetabulum 90.

Figure 4A:
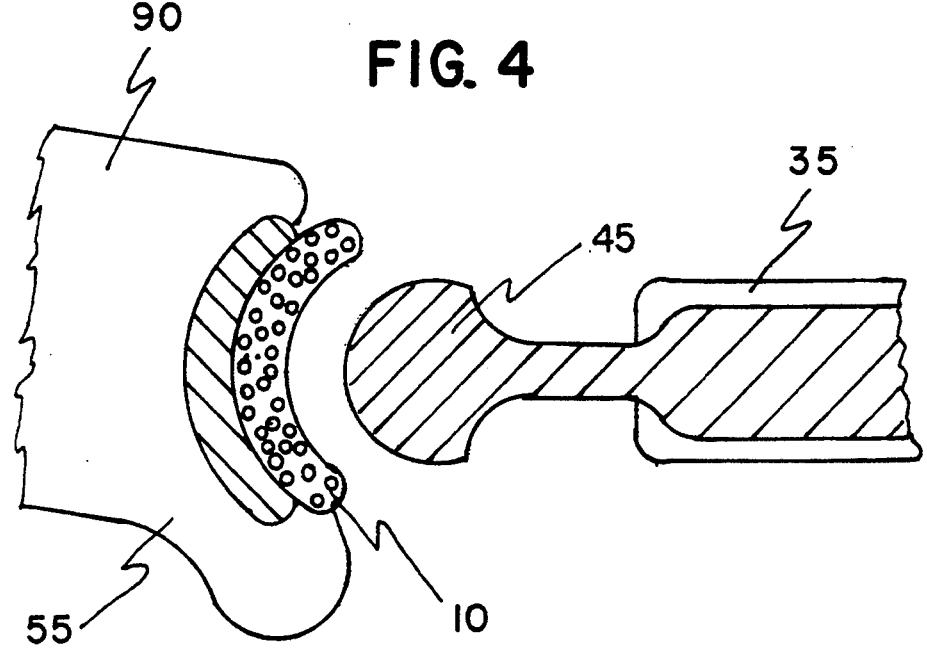
FIG. 4A is a side view of a hip arthroplasty with cartilage replacement pads.

FIG. 4A is a side view of a hip arthroplasty. The cartilage replacement pad 10 is inserted between the femoral component 45 of the prosthesis and the acetabular component 55 of the prosthesis.

Figure 5:
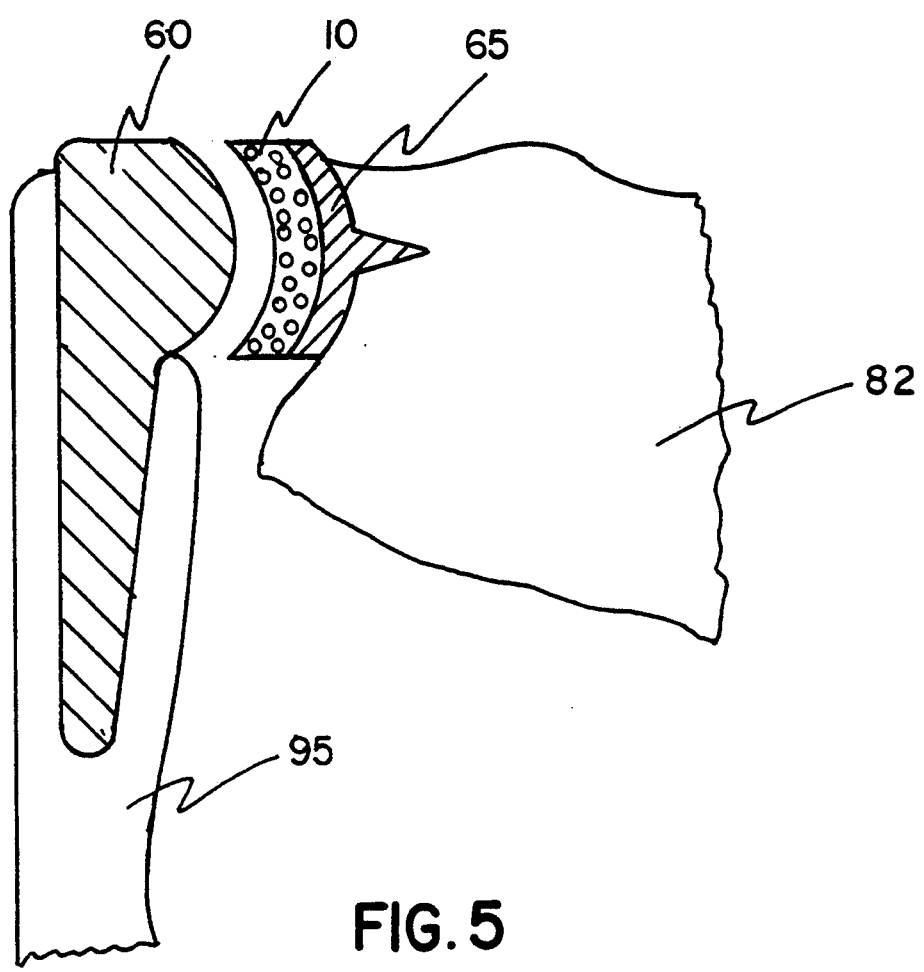
FIG. 5 is a frontal view of a shoulder arthroplasty with cartilage replacement pads.

FIG. 5 is a frontal view of a shoulder arthroplasty. The cartilage replacement pad 10 is inserted between the humeral component 60 and the glenoid component 65 of the prosthesis and locked into the glenoid component via a similar mechanism. The humeral component 60 is inserted into the humerus 95 and the glenoid component is secured to the scapula 82.

Figure 6:
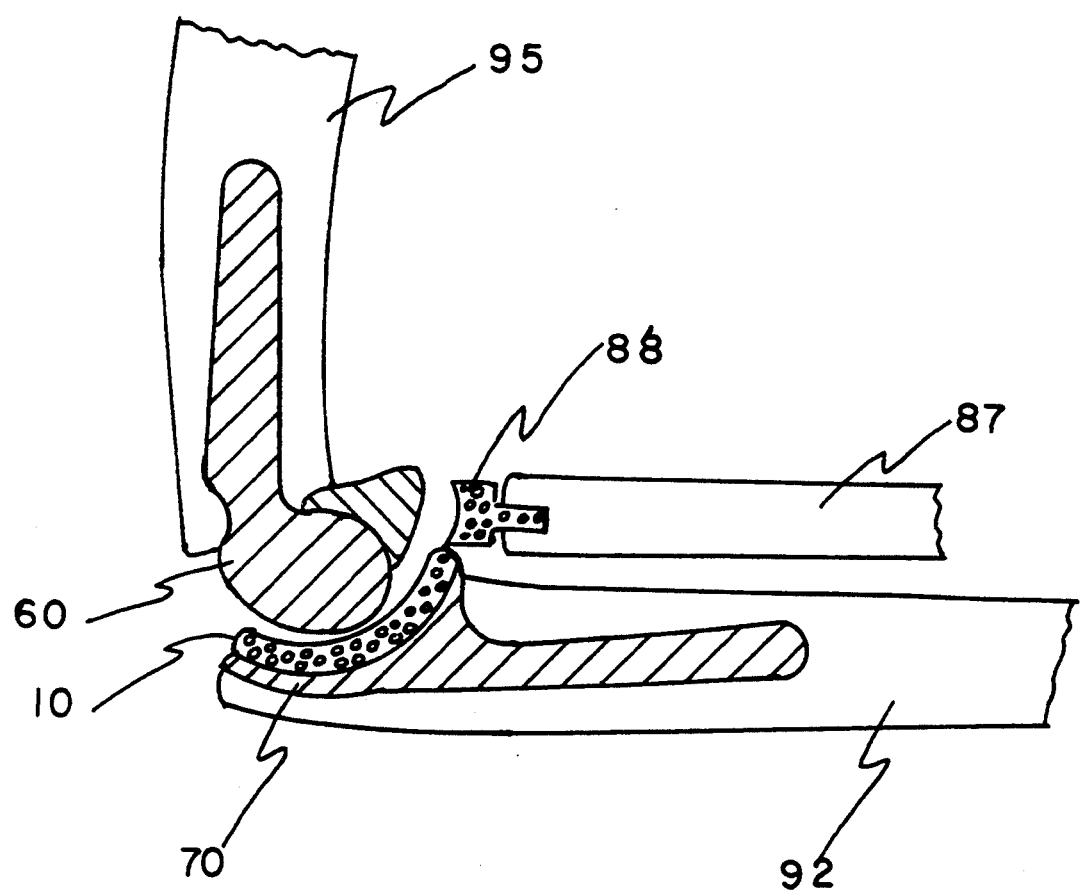
FIG. 6 is a side view of an elbow arthroplasty with cartilage replacement pads.

FIG. 6 is a side view of an elbow arthroplasty. The cartilage replacement pad 10 is inserted between the humeral component 60 of the prosthesis and the ulnar component 70 of the prosthesis and is an integral part of the ulnar component. The humeral component is inserted into the humerus 95 and the ulnar component is inserted into the ulna 92. Radial head component 88 of the prosthesis is inserted into radius 87 and rests next to the cartilage replacement pad 10 at a point above the ulnar component 70.

While there have been described what are at present considered to be the preferred embodiments of this invention, it will be obvious to those skilled in the art that various changes and modifications may be made therein without departing from the invention and it is, therefore, aimed to cover all such changes and modifications as fall within the true spirit and scope of the invention.

What is claimed is:

1. An implantable cartilage replacement apparatus comprising:
    a pad of pliable and compliant shock absorbing material with a hollow interior;
    load bearing material which fills the interior of said pad, and moves in response to varying load vectors applied to said pad; wherein said load bearing material further comprises numerous, small ball bearings of surgical-grade stainless steel; and
    wherein, said pad with said load bearing material is capable of self-modulation, congruency and shock absorbency in a manner similar to actual cartilage.

2. The apparatus of claim 1, wherein said pad is a plastic material.

3. The apparatus of claim 2, wherein said load bearing material further comprises a gelatinous fluid capable of shifting positions within said pad as varying load vectors are applied.

4. The apparatus in claim 3, wherein said plastic pad is ultra high molecular weight polyethylene plastic.

5. The apparatus in claim 2, wherein said pad further comprises a post for securing said pad in place.

6. The apparatus in claim 2, wherein said pad further comprises an apron for securing said pad in place.

7. The apparatus in claim 2, wherein said pad is shaped and dimensioned to be used for a meniscal cartilage replacement to replace diseased and injured meniscal cartilage in an otherwise structural sound knee.

8. The apparatus in claim 2 wherein said pad is shaped and dimensioned to be used as a bearing surface for total joint arthroplasty of the group having the members hip, knee, shoulder, elbow and ankle.

9. The apparatus in claim 2 wherein said pad is shaped and dimensioned to be used as a revision bearing surface for an existing total joint arthroplasty, which is otherwise structurally intact yet exhibiting damage to the existing bearing surface, wherein said pad provides an exchange revision arthroplasty of the bearing surface without disturbing the solidly anchored metal backed components where said pad extends the lifetime of the arthroplasty and prevents the effects of the destructive particulate debris.

* * * * *